United States Patent [19]

Fusee

[11] 4,371,611
[45] * Feb. 1, 1983

[54] ENZYMATIC DIAGNOSTIC COMPOSITION

[75] Inventor: Murray C. Fusee, Ellicott City, Md.

[73] Assignee: W. R. Grace & Co., New York, N.Y.

[ * ] Notice: The portion of the term of this patent subsequent to Oct. 7, 1997, has been disclaimed.

[21] Appl. No.: 189,994

[22] Filed: Sep. 23, 1980

Related U.S. Application Data

[63] Continuation-in-part of Ser. No. 931,334, Aug. 7, 1978, Pat. No. 4,226,935.

[51] Int. Cl.³ .................. C12Q 1/00; C12Q 1/50; C12N 11/06
[52] U.S. Cl. ........................... 435/14; 435/4; 435/15; 435/17; 435/21; 435/26; 435/181
[58] Field of Search .................. 435/4, 14, 15, 17, 21, 435/26, 171, 175, 180, 181, 182

[56] References Cited

U.S. PATENT DOCUMENTS

| | | | |
|---|---|---|---|
| 3,574,062 | 4/1971 | Sato | 435/177 |
| 3,705,084 | 12/1972 | Reynolds | 435/180 |
| 3,838,011 | 9/1974 | Hagen et al. | 435/4 |
| 3,905,923 | 9/1975 | Klug | 435/182 |
| 3,928,138 | 12/1975 | Wood et al. | 435/182 |
| 3,929,574 | 12/1975 | Wood et al. | 435/180 |
| 4,094,744 | 6/1978 | Hartdegen et al. | 435/180 |
| 4,095,948 | 6/1978 | Hunziker | 435/10 |
| 4,098,645 | 7/1978 | Hartdegen et al. | 435/182 |
| 4,102,742 | 7/1978 | Klose et al. | 435/14 |
| 4,226,935 | 10/1980 | Fusee | 435/14 |
| 4,250,267 | 2/1981 | Hartdegen et al. | 435/317 |

FOREIGN PATENT DOCUMENTS 1216512 12/1970 United Kingdom .
1302706 1/1973 United Kingdom .

OTHER PUBLICATIONS

Mosbach et al., "Matrix-bound Enzymes II Matrix-bound Two-enzyme System," *Chem. Abstracts*, vol. 74, No. 5, p. 48, (1971), Absts. No. 19778i.

Mosbach et al., "Matrix-bound Enzymes I, Use of Different Acrylic Copolymers as Matrixes," *Chem. Abstracts*, vol. 74, No. 5, p. 48 (1971), Absts. No. 19777h.

*Primary Examiner*—Thomas G. Wiseman
*Attorney, Agent, or Firm*—Philip M. Pippenger

[57] ABSTRACT

Disclosed herein is a method for binding enzymes comprising reacting either a synthetic or a natural polymer containing carboxyl and amino groups with an excess of a urethane prepolymer followed by coupling of an enzyme thereto by use of a carbodiimide. The product of the process is also described as well as the use thereof in analyzing blood fluids. The invention is particularly adapted to binding hexokinase and glucose-6-phosphate dehydrogenase to determine creatine phosphokinase (CPK) in human blood.

34 Claims, 1 Drawing Figure

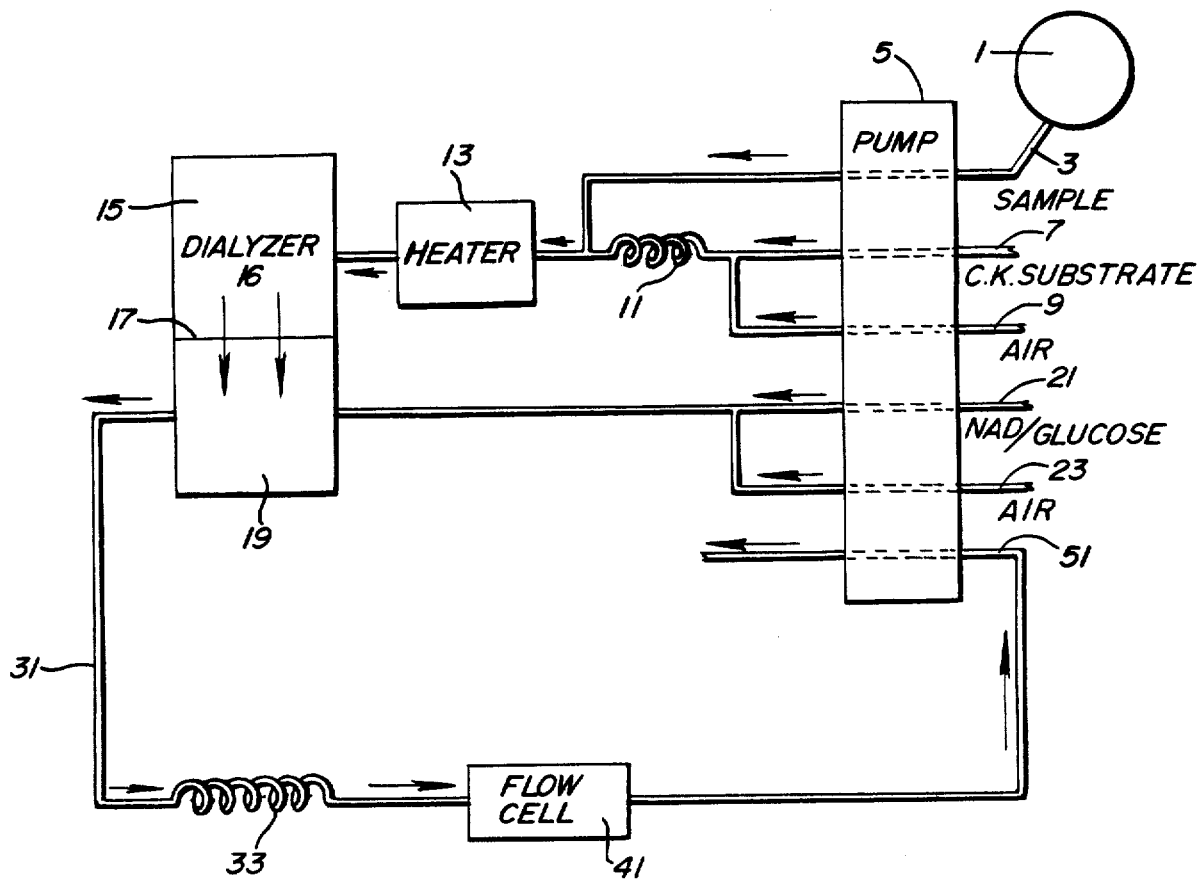

ENZYMATIC DIAGNOSTIC COMPOSITION

CROSS-REFERENCE TO RELATED APPLICATIONS

This is a continuation-in-part of co-pending application U.S. Ser. No. 931,334, U.S. Pat. No. 4,226,935, filed on Aug. 7, 1978.

Co-pending application Ser. No. 743,035, U.S. Pat. No. 4,098,645, describes a process whereby enzymes are dissolved in hydrophilic urethane prepolymers, and the resulting mixture is cured under foaming or non-foaming conditions to yield solid foams or films containing the bound enzyme in active form. Co-pending application Ser. No. 362,488 describes a process wherein the enzymes are dissolved in water and the aqueous solution is used to foam a hydrophilic urethane prepolymer resulting in a polyurethane foam containing bound enzymes in active form. Co-pending application Ser. No. 749,430, U.S. Pat. No. 4,094,744, describes admixing enzymes directly with a hydrophilic urethane prepolymer and dispersing the solution in water to form a solution or dispersion of the enzymes bound to water-soluble (or dispersible) polyurethanes. U.S. Pat. No. 3,929,574 describes the use of polyurethane foams containing active bound enzymes in various test procedures as well as reactions where bound enzyme foams were used to convert a substrate into the desired product, e.g., hydrolysis of penicillin V to penicillin G using penicillin amidase as the bound enzyme.

BACKGROUND OF THE INVENTION

The present invention relates to a method for immobilizing enzymes and to the product thereof as well as its uses. More particularly, the present invention relates to a method whereby enzymes are immobilized on a polyurethane foam or non-foamed substrate by means of an amino acid and/or protein bridging or coupling compound.

The use of enzymatic reactions in chemical analysis has become increasingly important in recent years, particularly with regard to the analysis of biological substances such as blood and other body fluids. Accordingly, numerous references describe the binding of enzymes using a wide number of substrates.

The use of polyurethane substrates is described in the references cited above. In U.S. Pat. No. 3,574,062 a system is described wherein a polyester polyurethane foam is used to bind enzymes via a complex procedure involving the use of amino acids and proteins. Schematically the product can be represented as follows:

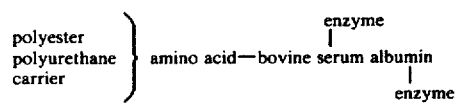

U.S. Pat. No. 3,830,699 describes the binding of enzymes to polyacrylonitrile polymers by an intermediate reaction of the nitrile groups with an alcohol and HCl to form an imidoester followed by coupling with an enzyme. In a journal article by Lee et al. (Biochimie, 1976, 58, 489-497) enzymes are coupled to collagen using an intermediate reaction between a carbodiimide designated as EDC, i.e., 1-ethyl-3(3-dimethylaminopropyl) carbodiimide-HCl, and functional groups on the collagen surface. Subsequently, the "activated" collagen is reacted with an enzyme. The reference indicates that the procedure is applicable to numerous enzymes, e.g., hexokinase. The use of carbodiimide in binding enzymes is also described in Chemical Abstracts references 74, 19777h and 19778j wherein acrylamide-acrylic acid copolymers are reacted with a water-soluble carbodiimide followed by reaction with an aqueous enzyme solution. Enzymes employed are trypsin and a combination of hexokinase with glucose-6-phosphate dehydrogenase.

DESCRIPTION OF THE INVENTION

The invention is a diagnostic composition comprising an enzyme, or mixture of enzymes, bound in biologically-active form to a carboxylated poly(ureaurethane) matrix having oxyalkylene backbone segments wherein at least 60 mole percent of the oxyalkylene units are oxyethylene. The enzymes are bonded to at least one exterior surface of said matrix. The diagnostic composition is prepared by reacting an amino acid with an excess of urethane prepolymer to form a carboxylated urethane prepolymer, i.e., amine and urethane groups react to form a prepolymer which has free carboxyl groups situated internally along the polymer chain, said prepolymer being terminated with isocyanate groups. The carboxylated prepolymer is cured and an enzyme is coupled thereto by use of a carbodiimide.

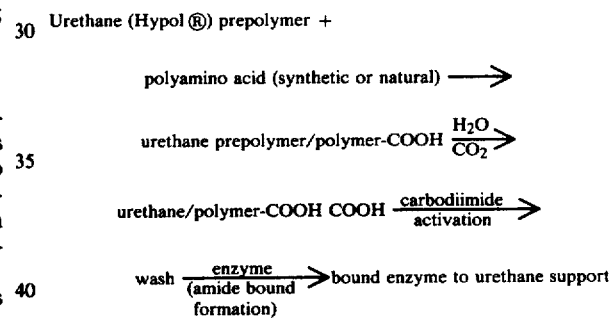

In describing the invention the term "amino acid" is intended to designate primarily "polymeric" amino acids, i.e., natural or synthetic polymers containing both carboxyl and amino groups, although for comparative purposes reference is also made to "monomeric" amino acids, e.g., glycine, leucine, phenyl alanine, etc.

The term "diagnostic composition" is intended to designate polyurethane films, foams or other solid polyurethane articles wherein one or more enzymes are bound to at least one exterior surface thereof rather than being distributed relatively uniformly throughout the polymer. The term "NAD(P)" means nicotinamide adenine dinucleotide and/or nicotinamide adenine dinucleotide phosphate.

The diagnostic composition is used to analyze various biological materials, i.e., human body fluids, to determine various components therein. For example, the diagnostic composition can be prepared in the form of several tubes, the first tube having hexokinase bound to the interior surface thereof and the second tube having glucose-6-phosphate dehydrogenase bound to the interior surface thereof. A sample of human blood serum in admixture with nicotinamide adenine dinucleotide (NAD), creatine phosphate, glucose, $Mg^{++}$, and adenosine diphosphate is passed through said tubes to provide a method of quantitatively determining the amount of creatine phosphokinase present in the sample. In the diagnostic reaction the enzymes serve to catalyze reaction between the components of the aqueous solution to provide NADH which is directly proportional to the amount of creatine phosphokinase present in the sample tested. The NADH level is read photometrically.

The preceding diagnostic reaction can be illustrated schematically as follows:

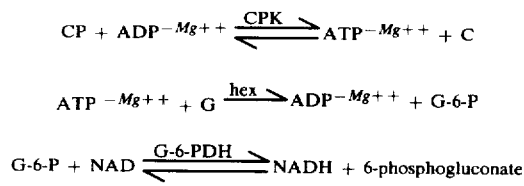

In the above sequence of reactions, the abbreviations used are as follows: CP (creatine phosphate), ADP (adenosine disphosphate), CPK (creatine phosphokinase), ATP (adenosine triphosphate), G-6-P (glucose-6-phosphate), NAD (nicotinamide adenine dinucleotide), G-6-PDH (glucose-6-phosphate dehydrogenase) and G (glucose).

In the above example the two tubes can be replaced by a single tube having a mixture of enzymes bound therein. Also, either the single or dual system of tubes can be used to analyze for ATP, glucose, glucose-6-phosphate, and NAD or NADP (nicotinamide adenine dinucleotide phosphate).

Additionally, by varying the reactants involved, the hexokinase/G-6-PDH tubes can be used together or separately to analyze for the following materials.

| Material to be Analyzed | Reagents |
| --- | --- |
| ADP | $Mg^{++}$, CP, CK, G, NAD(P) |
| CP | $Mg^{++}$, ADP, CK, G, NAD(P) |
| ATP | $Mg^{++}$, G, NAD(P) |
| G | $Mg^{++}$, ATP, NAD(P) |
| G-6-P | NAD(P) |
| NAD(P) | G-6-P |
| glucose-1-phosphate | phosphoglucomutase, NAD(P) |
| fructose-6-P | phosphoglucose isomerase, NAD(P) |
| myokinase | (2)ADP, $Mg^{++}$, G, NAD(P) (determine ATP produced) |
| phosphoglucose isomerase | fructose-6-phosphate, NAD(P) |
| galactokinase | ATP, $Mg^{++}$, galactose, glucose, NAD(P) (measure the reduction in ATP level) |

In carrying out the above analysis, the amounts of reagents to be used to maximize the sensitivity of any particular method can readily be determined by routine trials using various amounts of the reagents.

In preparing the diagnostic composition the urethane prepolymer is reacted with an amino acid using an excess amount of the prepolymer (in relation to the $-NH_2$ groups on the amino acid) so that the $NCO/NH_2$ ratio is from about 100/1 to about 4/1. Due to the difference in reactivity between the amino groups and the carboxyl groups, the amino groups are believed to preferentially react with the NCO groups of the prepolymer with each primary amino group having the capacity to react with two NCO groups and each secondary amino group having the capacity to react with one NCO. The resulting product can be considered as a chain-extended urethane prepolymer having the amino group bonded into the chain with the carboxyl groups pendant therefrom. The prepolymer/amino acid reaction can be carried out in the presence of solvents which dissolve or are miscible with one or both reactants, e.g., ethyl alcohol or ethyl acetate. The reaction is generally carried out at a temperature of from about 20° C. to about 30° C. Amino acids which may be used include bovine serum albumin, poly-L-alanine and, as an example of a hydrolized natural polymer containing both amine and carboxyl functionalities, gelatin, as well as the following monomeric amino acids for comparative purposes; phenyl alanine, glycine, α-amino isobutyric acid, 12-aminododecanoic acid, p-aminophenylacetic acid, and p-aminohippuric acid.

The carboxylated prepolymer is cured by exposure to any of the commonly used curing agents such as amines or water. Preferably, curing is accomplished by exposure to water vapor. The speed of the curing reaction with water is important in that the water/NCO reaction liberates $CO_2$ which tends to introduce porosity into the polymer matrix. If $CO_2$ generation is relatively fast the prepolymer can be converted into a foam, whereas slower rates tend to produce non-foamed structures frequently referred to as films. The techniques for preparing either films or foams and controlling the rate of $CO_2$ generation are well known in the art and do not form part of the present invention.

Prior to curing the carboxylated prepolymer is a viscous liquid which can be easily shaped as by coating on a metal rod, molding, or allowing the prepolymer to spread over a flat surface to form a film.

Following the curing and optional shaping steps, the carboxylated cured polymer matrix is reacted with an activating agent having one or more functional groups reactive with the carboxyl groups to form covalent bonds subject to displacement by primary or secondary amine groups of an enzyme. Examples of suitable activating agents include carbodiimides, acid chlorides, succinimides, and acetylation with methanol and HCl followed by hydrazide formation using hydrazine. Woodward's reagent "K" is also suitable. Specific examples of the above components include: carbodiimides:

1-ethyl-3-(3-dimethylaminopropyl)-carbodiimide, N,N'-dicyclohexylcarbodiimide, 1-cyclohexyl-3-(2-morpholinoethyl)-carbodiimide metho-p-toluenesulfonate, diphenyl carbodiimide; Woodward's reagent K. i.e., N-ethyl-5-phenylisoxazolium-3'-sulfonate; acid chlorides, e.g., thionyl chloride; and succinimides, e.g., N-hydroxysuccinimide.

Conditions for reacting the above activating agents with carboxyl groups are well known. For carbodiimides, the reaction is generally carried out at an acid pH preferably around 3 to about 6, and at a temperature of less than 10° C. and preferably between 0° and 5° C. The carbodiimide can be employed in aqueous or non-aqueous solution, and a sufficient amount should be employed to react with all carboxyl groups present, i.e., the $-N=C=N-/-COOH$ ratio should be at least 1/1 and preferably from about 6/1 to about 60/1. Regarding the temperature range set forth above, it will be apparent that freezing of the reagents should be avoided. It is believed that the carbodiimide or other activating agent reacts with the carboxyl groups to form a relatively labile linkage which can be displaced by amino groups present on proteins such as enzymes. The linkage is also unstable in the presence of heat and therefore the reaction temperatures should be less than 10° C. as specified above where a carbodiimide is employed.

The "activated" polymer is subsequently reacted with an aqueous solution of enzyme. The reaction is carried out under alkaline conditions and preferably at a pH of from about 7.5 to about 9.0. The amount of enzyme employed varies with regard to the number of amino groups present in the enzyme. For hexokinase it has been found that, based on the weight of the activated polymer, from about 0.2 to about 2.0% enzyme should be present in the aqueous solution, i.e., this amount of enzyme should be dissolved in the aqueous solution contacted with the activated polymer. Similarly, for glucose-6-phosphate dehydrogenase from about 0.05 to about 0.5 weight percent enzyme should be employed. For each particular enzyme the optimum binding level can be determined by a series of runs at different levels followed by analysis of the amount of enzyme bound. In addition to the enzymes described above other enzymes which can be employed are glycerol dehydrogenase, lipase, glucose oxidase, galactose oxidase, lactate dehydrogenase, glucose dehydrogenase, malate dehydrogenase, peroxidase, catalase, creatine phosphokinase, uricase, urease, alcohol dehydrogenase, cholesterol oxidase, α-amylase, β-amylase, glucoamylase, lactase, glucose isomerase, trypsin, chymotrypsin, pepsin, papain, bromelain, hydrogenase, diaphorase, dextranase, rennin, cellulase, cellobiase, glycerol kinase, pyruvate kinase, pectinase, adenylate kinase, and lysozyme.

The temperature during the enzyme binding reaction should be from about 4° C. to about 20° C., and preferably from about 4° C. to about 10° C. It has been demonstrated that the use of more than one layer of carboxylated polymer does not confer significant advantages in view of the amount of bound enzyme activity. It is therefore believed that in solid non-foamed products the enzyme is bound primarily at the surface of the polymer matrix rather than internally. Additionally, the introduction of bubbles (e.g., of air or other gases) into the enzyme solution contacted with the activated tubes has been found to increase the amount of enzyme bound thereto.

Numerous applications for bound or immobilized enzymes are known. The present invention is especially suited for the analysis of creatine phosphokinase (CPK). Such analysis can be carried out by preparing a single polyurethane tube having a mixture of hexokinase and glucose-6-phosphate dehydrogenase (G6PDH) bound on the interior surface thereof. With reference to the FIGURE there is described, schematically, a mechanical system for continuous analyses of a large number of serum samples. Such devices are well known, e.g., the Technicon AAII by Technicon Corp., Tarrytown, N.Y. In the FIGURE, the serum sample is placed in sample tray I, which delivers the sample through line 3 to unified pumping head 5 at a rate of 0.32 cc/min. Simultaneously a mixture of creatine phosphate, adenosine diphosphate, $Mg^{++}$ and N-acetylcysteine is monitored (0.60 cc/min.) through line 7 into pumping head 5, and air is monitored through line 9 at a rate of 0.32 cc/min. N-acetylcysteine (N-Ac) is required as a CPK activator. The air and CP/ADP/N-Ac/$Mg^{++}$ streams are mixed in coil 11 and subsequently combined with sample stream 3. The unified stream is passed through heater bath 13 wherein the stream is heated to about 37° C. Thereafter the heated stream is passed into the upper chamber 15 of dialyzer 16. Any CPK present in the sample catalyzes reaction between the CP and ADP to produce ATP and creatine. The ADP, ATP and creatine diffuse through membrane 17 into the second chamber 19 of dialyzer 16. The second chamber of the dialyzer also contains NAD/glucose/$Mg^{++}$ mixture injected into the system through line 21 (1.00 cc/min.) via pumping head 5. The NAD/glucose/$Mg^{++}$ mixture is mixed with air injected via line 23 (0.32 cc/min.) through pumping head 5. The NAD/glucose $Mg^{++}$ air stream procedes via line 25 into dialyzer chamber 19 and is combined with ATP from the upper chamber 15. Thereafter the unified stream is passed through line 31 through coiled tube 33 and flow cell 41. Thereafter the sample is passed through line 51 and pumping head 5 to a waste receptacle.

Tube 33 is prepared by the present invention and contains an admixture of hexokinase and G6PDH immobilized on the surface thereof. The enzymes catalyze reaction of ATP, glucose, $Mg^{++}$, NAD(P) and G6P to produce NAD(P)H. The level of NAD(P)H is read photometrically at 340 nanometers in flow cell 41 to quantitatively determine the amount of CPK present in the original sample.

Generally, the isocyanate-terminated prepolymers used in the practice of this invention are the reaction product of a polyoxyalkylene polyol and a polyisocyanate. The OH equivalent weight of the polyoxyalkylene polyols useful in this invention is from about 350 to about 4,000. Said polyols should have at least 60 mole percent oxyethylene in the oxyalkylene portion (exclusive of the initiator) in order to provide a prepolymer with good hydrophilicity. Particularly good results are obtained with polyol precursors having an OH equivalent weight which is somewhat greater than 350, e.g., 500 up to 2,000.

The polyoxyalkylene chains of the prepolymers used in this invention preferably contain mostly or entirely oxyethylene units (e.g., greater than 70 mole percent) but copolymers, terpolymers, etc., containing a minor amount of oxypropylene, oxy-1-2-butylene or oxy-1-4-butylene units are not detrimental and may provide desirable properties, e.g., increasing the flexibility of the cured polymer. The copolymers can be random or block copolymers, as is well known in the art. It is thus useful for the purpose of the invention to employ random or block copolymer oxyalkylene chains in which a majority (greater than 60 mole percent) of the repeating units are oxyethylene. Likewise, simple mixtures of polyoxyethylene polyols with other polyols to make the prepolymers of this invention, and mixtures of oxyethylene containing prepolymers can be used, provided that the total oxyethylene units in the cured polymer will always be at least 60 mole percent. These various mixtures and copolymers can be selected with a view toward varying the amount of hydrophilicity, flexibility and stretchability or conformability of the cured polymer.

The isocyanate components of the prepolymers of this invention are derived from an aliphatic, aromatic or aralkyl polyisocyanate, preferably a diisocyanate such as tolylene diisocyanate (TDI), xylene diisocyanate (XDI), naphthalene diisocyanate, 4,4'-diphenylmethane diisocyanate (MDI), phenylene diisocyanate, "PAPI," etc. Suitable isomers of these diisocyanates can also be used or mixtures thereof, e.g., 2,4-2,6-TDI, 1,5-naphthalene diisocyanate, n-phenylene diisocyanate, as well as those diisocyanates listed in *Polyurethanes: Chemistry* and *Technology* by Saunders & Frisch, Part 1, Interscience Publishers, New York (1962), p. 348, and *Encyclopedia of Chemical Technology* by Kirk and Othmer, Second Ed., Vol. 12, pp. 46, 47, Interscience Publishers, New York (1967).

In the following examples the following terms have the indicated meaning:

| | |
|---|---|
| PAPI | a polyaryl polyisocynate available from the Upjohn Co. |
| EDC | 1-ethyl-3-(3-dimehylaminopropyl)-carbodiimide hydrochloride having a structural formula as follows: $CH_3CH_2N=C=NCH_2CH_2CH_2N(CH_3)_2 \cdot HCl$ |
| PABA | p-aminobenzoic acid |
| HK | hexokinase obtained from yeast. In the examples the hexokinase was obtained from Worthington Biochemical Co., Freehold, New Jersey, as a lyophilized powder having a specific activity of 138 units/mg. wherein 1 unit of activity is taken to be the amount of enzyme which reduces 1.0 μmole of NAD/minute at 30° C., pH 8.0 |
| G6PDH | glucose-6-phosphate dehydrogenase. In the examples the G6PDH was obtained from Sigma Chemical Co., St. Louis, Missouri, as a lyophilized powder having a specific activity of 500 NAD units/mg, i.e., 1 unit of activity will oxidize 1.0 μmole of glucose-6-phosphate to 6-phosphogluconate per minute at pH 7.4 and 25° C., using NAD as the coenzyme. |
| ADP and ATP | adenosine diphosphate and adenosine triphosphate |
| NAD and NADH | nicotinamide adenine dinucleotide and reduced nicotinamide adenine dinucleotide |
| NADP | nicotinamide adenine dinucleotide phosphate |

Prepolymer A was prepared by admixing 2 molar equivalents of polyethylene glycol having an average molecular weight of 1,000 and 0.66 molar equivalents of trimethylolpropane. The admixture was dried at 100°–110° C. under a pressure of 5–15 Torr to remove water. The dried mixture was slowly added over a period of about 1 hour to a vessel containing 5.52 molar equivalents of toluene diisocyanate (TDI). While stirring the TDI and polyol mixture the temperature was maintained at 45°–65° C. during the addition and for several additional hours thereafter. During this reaction period chain-extension occurred in the prepolymer. Subsequently, an additional 0.78 molar equivalent of TDI was added with stirring over a period of from about 0.5–1 hour while maintaining the temperature at about 60° C.

Prepolymer B is a mixture of 80 parts by weight of Prepolymer A with 20 parts by weight of PAPI.

Prepolymer C is Sanprene WE-108X (Sanyo Chemical Industries Ltd., Kyoto, Japan) and contains a polyol component having a molar ethylene oxide/propylene oxide ratio of about 5/1 and a molecular weight of about 3000–3500.

Prepolymer D is a mixture of 80 parts by weight of Prepolymer C with 20 parts by weight of PAPI.

Prepolymer E is prepolymer XD-1421 (Dow Chemical Co., Midland, Mich. and contains a polyol having a molar ethylene oxide/propylene oxide ratio of about 3/1 and having a molecular weight of about 5,000.

Prepolymer F is a mixture of about 80 parts by weight of Prepolymer E and 20 parts by weight of PAPI.

EXAMPLE 1

Preparation of Polyurethane Tubes Having HK and G6PDH Bound to the Internal Surface Thereof One percent (wt/wt) PABA was admixed with a mixture of 80 wt. % Prepolymer C and 20 wt. % PAPI. The mixture was allowed to react for about 15 minutes and was then coated uniformly over the surface of a steel rod (30 cm. long) using about 30 mg. of the prepolymer/PABA mixture. The mixture was cured by exposure to humid air (90% relative humidity) for about 30 minutes. Subsequently, a second coat was applied by admixing Prepolymer A with an equal portion by weight of acetone and applying 15 mg of this admixture to the first coating. The second coating was cured in essentially the same manner as the first coating. Additional coats of acetone/Prepolymer A were applied until the resulting laminated tube had an inside diameter of approximately 0.0625 inches and an outside diameter of approximately 0.375 inches. 35 tubes were prepared as described above.

The tubes were removed from the metal rods by soaking in water. Thereafter 5 cc of EDC solution was recycled through each tube for approximately 5 hours at a temperature of about 4° C. The recycle rate was about 1 cc/min. The EDC solution contained 40 mg of EDC per cc in water, with pH adjusted to 4.5 using HCl. Following the 5-hour recycle stage, each tube was washed for about 10 minutes by cycling 0.1 M K phosphate buffer (pH 7.6) through each tube at a rate of about 5–10 cc/min.

Enzyme was bound to each tube by dissolving 826 units of HK and 350 units of G6PDH in sufficient K phosphate buffer (as described above) to yield an aqueous solution with total volume of 1.5 cc.

For each tube an enzyme solution prepared as described was recycled (∼1 cc/min) through the tube at 4° C. for about 1 hour followed by storage overnight (at 4° C.) with the enzyme solution in contact with the interior layer of the tube. Subsequently, each tube was washed with 1 M K phosphate buffer (pH 7.0) for about 1 hour.

To store the tubes after preparation, or after use, each tube is rinsed for several minutes with 7.0 tris buffer solution (0.10 M) to wash out any substrate. The tris buffer is subsequently replaced with 2 M NH4SO4 solution containing 0.10 M K phosphate buffer, pH 7.0. For long storage periods (e.g., in excess of 24 hours), the tubes filled with $(NH_4)_2SO_4$ solution as described are preferably placed in a container also filled with a similar solution, and the container is then sealed to prevent evaporation. The tubes are stored in a refrigerator at 4° C.

In determining the enzyme activity in the tubes, the co-bound G6PDH is used to assay for HK activity. Using tris buffer (0.10 M, pH 7.5) containing $MgCl_2 \cdot 6H_2O$ (3.0 mg/cc), ATP (1.33 mg/cc), and NAD (1.0 mg/cc), approximately 4 cc. of the above substrate solution is pumped through the tube being analyzed at room temperature and a flow rate of 1 cc/min. The effluent is collected, mixed and the NADH level is read in a spectrophotometer at 340 nm. For HK the optical density (OD) is 0.410±0.164 based on analysis of 35 tubes each with a length of about 30 cm.

G6PDH is determined using the same tris buffer as above containing glucose-6-phosphate (0.83 mg/cc) and NAD (0.25 mg/cc). Four cc of the substrate solution is passed through the tube being analyzed at a flow rate of 1 cc/min at room temperature. The effluent is collected, mixed and NADH is read in a spectrophotometer at 350 nm. The OD level for G6PDH is about 0.323±0.113 based on analysis of 35 tubes each having a length of about 30 cm.

For purposes of the comparisons made in Example 2, the OD levels for HK and G6PDH were used as standards.

EXAMPLE 2

To determine the effect of other parameters on performance of the bound enzyme tubes, tubes (each tube was 30 cm in length) were prepared using the technique described in Example 1 but varying one or more parameters. In each case the bound HK and G6PDH activities were determined.

Two tubes were prepared using increased amounts of HK amounting to 1239 units/30 cm tube. The HK level was 0.625±0.065, while the G6PDH level was 0.313±0.013. Two tubes were prepared using increased G6PDH levels of 667 units/30 cm tube (HK loading=826 units). The HK level was 0.630±0.050, and G6PDH was 0.445±0.

One tube was prepared using 2 mg/cc of glucose in the aqueous enzyme solution in addition to the other ingredients present therein as described in Example 1. Bound HK activity was 0.565, and G6PDH was 0.309. Similarly, 1 mg/cc of NAD was added to the aqueous enzyme solution (in place of the glucose). The single tube prepared showed bound HK activity of 0.760 and G6PDH of 0.354. Using a combination of 2 mg/cc of glucose and 1 mg/cc of NAD in the enzyme solution, the single tube prepared showed bound HK activity of 0.878 and G6PDH of 0.424.

Tubes were prepared varying the EDC level described in Example 1. The results are set forth in the following table:

| EDC Level | Bound HK (O.D.) | Bound G6PDH (O.D.) |
|---|---|---|
| 1 mg/cc | 0.134 | 0.190 |
| 2 mg/cc | 0.415 | 0.260 |
| 4 mg/cc | 0.498 | 0.302 |
| 10 mg/cc | 0.316 ± 0.023 | 0.242 ± 0.004 |
| 20 mg/cc | 0.390 ± 0.083 | 0.211 ± 0.038 |

At levels of 10 and 20 mg/cc of EDC, two and three tubes were prepared respectively. Except for the 1 mg/cc level, the concentration of EDC did not appear to affect the enzyme activity of the tubes.

To determine the effect of the number of polymer layers containing PABA, 16 tubes were prepared using 1 coat and 14 tubes were prepared using 2 coats. The tubes having 1 inner coating containing PABA exhibited bound HK activity of 0.392±0.185 and G6PDH of 0.262±0.077. For tubes having 2 inner coats containing PABA, the bound HK activity was 0.371±0.153 and G6PDH was 0.270±0.096. It can be seen that use of a single PABA-containing inner layer results in approximately the same level of enzyme activity as two such layers, which indicates that the enzyme activities are bound primarily at the interior surface of the tubes.

A single tube was prepared wherein EDC was replaced with 40 mg/cc of 1-cyclohexyl-3-(2-morpholinoethyl)-carbodiimide metho-p-toluenesulphonate. On a molar basis the cyclohexyl carbodiimide was employed at a level of 0.094 molar as opposed to ~0.2 for the EDC. The bound HK activity was 0.050, and G6PDH was 0.167.

In another variation of the procedure of Example 1, a single tube was prepared using 1 weight percent PABA and 99 wt. % of Prepolymer C. The bound HK activity was 0.116, and G6PDH was 0.154. Six tubes were prepared using 1 wt. % PABA, and 99 wt. % Prepolymer B. The bound HK activity was 0.281±0.075, and the G6PDH level was 0.211±0.029. Single tubes were prepared using Prepolymer B as described immediately above and varying the amount of enzyme employed. The results were as follows:

| HK Units Added | G6PDH Units Added | Bound HK (OD) | Bound G6PDH (OD) |
|---|---|---|---|
| 413 | 192 | 0.138 | 0.157 |
| 275 | 128 | 0.120 | 0.158 |
| 826 | 230 | 0.188 | 0.179 |
| 826 | 115 | 0.180 | 0.168 |

From the above table it can be seen that variation in enzyme concentration produced a variation in the enzyme activity in the resulting tube.

A single tube was prepared using 99 wt. % Prepolymer A and 1 wt. % PABA. The bound HK activity was 0.376, and the G6PDH was 0.217.

The procedure of Example 1 was varied by using a mixture of 90 wt. % Prepolymer A and 10 wt. % bovine serum albumin. The mixture was allowed to react for about 15 minutes and was subsequently used to prepare a tube as in Example 1. The bound Hk activity was 0.171, and the G6PDH level was 0.221. Using BSA, a second tube was prepared using 10 wt. % BSA, 1 wt. % PABA and 89 wt. % Prepolymer A. The BSA and PABA were admixed with the Prepolymer A, and the mixture was allowed to react for about 15 minutes followed by tube formation as described in Example 1. The bound HK activity was 0.257, and the G6PDH level was 0.264.

A single tube was prepared using a mixture of 1 wt. % PABA with 99 wt. % Prepolymer E. The bound HK activity was 0.195, and the G6PDH level was 0.164.

Three tubes were prepared using a mixture of 1 wt. % PABA with 99 wt. % Prepolymer F. The bound HK activity was 0.562±0.083, and the G6PDH level was 0.269±0.005.

EXAMPLE 3

Comparative Example 2478 units of HK and 1050 units of G6PDH were admixed with 0.1 g of Prepolymer A, and the mixture was allowed to react for about 0.5 hour. The resulting mixture was applied to a 90 cm metal rod, cured, removed from the rod and stored as in Example 1. The bound HK activity (tube length=90 cm) was 0.022, and the G6PDH level was 0.027. Example 3 demonstrates that admixture of the dry powdered enzymes directly with the prepolymer does provide tubes with enzymatic activity, but such tubes provide significantly less activity than tubes prepared by the procedure of Example 1.

EXAMPLE 4

The procedure of Example 1 was followed to prepare tubes except that PABA was replaced with ~2%

(wt/wt) of gelatin (hydrolyzed collagen), and the prepolymer was Prepolymer A. The bound HK activity was 0.400, and the G6PDH level was 0.350 (tube length=30 cm).

EXAMPLE 5

The procedure of Example 1 was followed using various amino acids in place of PABA. The prepolymer employed was Prepolymer A. Analysis of the tubes (tube length=30 cm) yielded the following results:

| Amino Acid | HK | G6PDH |
|---|---|---|
| α-aminoisobutyric acid | 0.201 | 0.145 |
| p-aminohippuric acid | 0.322 | 0.284 |
| α-aminododecanoic acid | 0.361 | 0.257 |
| p-aminophenylacetic acid | 0.444 | 0.461 |

The following example was designed to illustrate the practice of the present invention by setting up a comparison between the activity of enzyme bound via the amine acid polymer and the activity of the enzyme bound via the amino acid monomer.

EXAMPLE 6

Three polyurethane tubes were made, each containing a different amino acid polymer, and compared to one made using an amino acid monomer as a control (p-aminobenzoic acid). Duplicate tubes for each test, including the control, were made. The three tests include:

Bovine serum albumin (Sigma, Cat #A-4503), gelatin (U.S.P.), and poly L-alanine (Sigma, Cat. #P-9128). Gelatin, which is an example of a hydrolyzed natural polymer containing both amine and carboxyl functionalities, was ground and sieved (125μ sieve) before use. Each polymer was mixed with Prepolymer A (anhydrous conditions) and allowed to react for one-half hour prior to application to scored metal rods (90 cm in length). Outer coats of Prepolymer A were then laminated by the procedure described in Example 1. The polyurethane tubes were then soaked off with deionized water and an aqueous solution of 1-ethyl-3-(-3-dimethylaminopropyl) carbodiimide-HCl (40 mg/cc, pH adjusted to 4.6) was introduced into each tube and the reaction allowed to continue for four hours at 4°–10° C. The tubes were then washed with cold pH 7.5 K phosphate buffer (0.1 M) for 45 minutes, then an enzyme solution (L-amino acid oxidase, Sigma, Type III, #A-8390, from Crotalus atrox venom) was pumped into each tube for subsequent binding overnight at 4°–10° C. The enzyme is a lyophilized product containing 45% protein and 55% glycine buffer salt. Each tube received ∼1 cc of enzyme solution which contained ∼0.8 units (where 1 unit activity=oxidative detamination of 1 μM of L-leucine per minute at pH 7.5 at 37° C.). After the overnight enzyme binding reaction, the tubes were washed with 0.1 M K phosphate buffer containing 0.1 M (NH4)2 at pH 7.5 for three hours to wash out any nonreacted enzyme. Each enzyme tube was then tested for activity against a sample containing 1 mg/cc L-leucine on a Technicon AutoAnalyzer II as described schematically in the FIGURE with the following modifications: line 3 was used to insert air at 0.32 cc/min; line 7 was used to insert "R-1" buffer at 0.60 cc/min; line 9 was used to insert the sample to be analyzed at 0.23 cc/min; line 21 was used to insert air at 0.32 cc/min; and line 23 was used to insert "R-2" buffer at 0.80 cc/min. Following passage of the reaction materials through enzyme tube 33 (containing L-amino acid oxidase) additional reagents "R-3" and "R-4" were added at the rate of 0.10 cc/min and 0.32 cc/min respectively. Thereafter the reaction stream passed through a 30-turn mixing coil (not shown) and was analyzed in a colorimeter at 505 nm. The reagents (R-1 through R-4) are described as follows:

R-1 and R-2: 0.1 M Glycine buffer (pH 7.5) with 1 cc/l Brij 35 added.

R-3: 186 mg/100 cc 4-aminoantipyrine (in Tris-citrate buffer, pH 7.5).

R-4: 50 mg/100 cc 2,4-dichlorophenol plus ∼4000 units/l horseradish peroxidase (in tris-citrate buffer, pH 7.5).

The overall reaction is as follows:

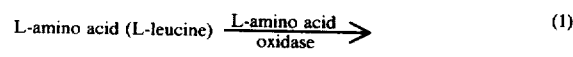

$$\text{L-amino acid (L-leucine)} \xrightarrow{\text{L-amino acid oxidase}} \quad (1)$$

$$\alpha\text{-keto acid} + NH_3 + H_2O_2$$

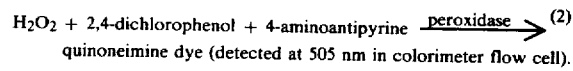

$$H_2O_2 + 2,4\text{-dichlorophenol} + 4\text{-aminoantipyrine} \xrightarrow{\text{peroxidase}} \quad (2)$$

quinoneimine dye (detected at 505 nm in colorimeter flow cell).

With the standard calibrator of the autoanalyzer set at 200, and the sampling cam was a 60 1/1, analyses of a 1 mg/cc L-leucine standard was performed with each tube, and the following results were recorded.

| Tube | Amino Acid Component | O.D. on AAII at 505 nm |
|---|---|---|
| A | Bovine serum albumin | 0.046 |
| B | Bovine serum albumin | 0.047 |
| C | Gelatin | 0.038 |
| D | Gelatin | 0.082 |
| E | Poly L-alanine | 0.010 |
| F | Poly L-alanine | 0.030 |
| G | p-aminobenzoic acid | 0.029 |
| H | p-aminobenzoic acid | 0.022 |

Even though a considerable amount of glycine was contained with the lyophilized L-amino acid oxidase samples during binding, some enzyme was bound (the amine group of glycine would be expected to compete for binding sites). The assay results point out the feasibility of using polymeric amino acids (either natural or synthetic) in conjunction with a polyurethane prepolymer. The results indicate that the polymeric amino acid tubes are at least as active as the p-aminobenzoic acid tubes.

Certainly reasonable variations and modifications within the scope of the present disclosure are possible, yet without departing from the reasonable scope and intended spirit thereof, as shown by the specification itself and by the claims here appended.

What is claimed is:

1. A diagnostic composition comprising a mixture of hexokinase and glucose-6-phosphate dehydrogenase bound in biologically-active form to a carboxylated poly(urea-urethane) polymer matrix having oxyalkylene backbone segments wherein at least 60 mole percent of the oxyalkylene units are oxyethylene, said carboxylated polymer prepared by reacting an excess of a polyoxyalkylene urethane prepolymer with a polymeric amino acid and wherein said enzymes are bonded to at least one exterior surface of said polymer matrix.

2. A composition as in claim 1 wherein the matrix is in the form of a foam.

3. A composition as in claim 1 wherein the matrix is in the form of a film.

4. A composition as in claim 1 wherein the matrix is in the form of a self-supporting tubular film having enzymes bound on the interior surface thereof.

5. A composition as in claim 1 wherein the backbone components are polyoxyethylene/polyoxypropylene copolymers.

6. A method for analyzing human body fluids comprising contacting a first aqueous solution of said body fluids with a mixture of hexokinase and glucose-6-phosphate dehydrogenase bound in biologically-active form to a carboxylated polyurethane polymer matrix, allowing said immobilized enzymes to catalyze reaction between the components of the first aqueous solution to form a second aqueous solution and determining the amount of at least one component of said second aqueous solution, said polymer comprising the reaction product of an excess of polyoxyalkylene urethane prepolymer with a polymeric amino acid.

7. A method as in claim 6 wherein the body fluid is analyzed to determine the presence of adenosine triphosphate.

8. A method as in claim 6 wherein the body fluid is analyzed to determine the presence of adenosine diphosphate.

9. A method as in claim 6 wherein the body fluid is analyzed to determine the presence of creatine phosphate.

10. A method as in claim 6 wherein the body fluid is analyzed to determine the presence of glucose.

11. A method as in claim 6 wherein the body fluid is analyzed to determine the presence of glucose-6-phosphate.

12. A method as in claim 6 wherein the body fluid is analyzed to determine the presence of nicotinamide adenine dinucleotide.

13. A method as in claim 6 wherein the body fluid is analyzed to determine the presence of nicotinamide adenine dinucleotide phosphate.

14. A method as in claim 6 wherein the body fluid is analyzed to determine the presence of glucose-1-phosphate.

15. A method as in claim 6 wherein the body fluid is analyzed to determine the presence of fructose-6-phosphate.

16. A method as in claim 6 wherein the body fluid is analyzed to determine the presence of myokinase.

17. A method as in claim 6 wherein the body fluid is analyzed to determine the presence of phosphoglucose isomerase.

18. A method as in claim 6 wherein the body fluid is analyzed to determine the presence of galactokinase.

19. A method as in claim 6 wherein the body fluid is analyzed to determine the presence of creatine phosphokinase.

20. A method as in claim 19 wherein the first aqueous solution comprises the body fluid to be tested, creatine phosphate, glucose, adenosine diphosphate, magnesium ions, and NAD or NAD phosphate, and the second aqueous solution comprises NADH or NADPH in an amount proportional to the creatine phosphokinase level in the body fluid tested.

21. A method as in claim 19 wherein the polymer matrix comprises, based on the total weight of said matrix and enzymes bound therein, from about 0.001 to about 1% of hexokinase and from about 0.001 to about 1% of glucose-6-phosphate dehydrogenase.

22. A method as in claim 19 wherein the polymer matrix is in the form of a foam.

23. A method as in claim 19 wherein the polymer matrix is a film.

24. A method as in claim 19 wherein the polymer matrix is a tubular self-supporting film.

25. A method as in claim 19 wherein the NADH or NADPH concentration is determined photometrically.

26. A method for binding enzymes comprising reacting polymeric amino acid with an excess of a polyoxyalkylene urethane prepolymer to form a carboxylated prepolymer, curing the carboxylated prepolymer and coupling an enzyme thereto by use of a carbodiimide.

27. A method as in claim 26 including the additional step of shaping the carboxylated prepolymer prior to curing.

28. A method as in claim 26 wherein the carboxylated prepolymer is cured to form a foam.

29. A method as in claim 26 wherein the carboxylated prepolymer is cured to form a film.

30. A method as in claim 26 wherein the enzyme employed is hexokinase.

31. A method as in claim 26 wherein the enzyme employed is glucose-6-phosphate dehydrogenase.

32. A method as in claim 26 wherein a mixture of hexokinase and glucose-6-phosphate dehydrogenase is employed.

33. The method as in claims 1 or 26 wherein said polymeric amino acid is selected from the group of either synthetic or natural polymers containing carboxyl and amino groups.

34. The method as in claim 33 wherein said carboxyl and amino group containing polymers are selected from the group comprising bovine serum albumin, poly L-alanine and gelatine.

* * * * *